United States Patent
McLaughlin et al.

[11] Patent Number: 5,746,207
[45] Date of Patent: May 5, 1998

[54] PROFILED BIOSIGNAL ELECTRODE DEVICE

[76] Inventors: James Andrew McLaughlin, 9 Hampton Court Village, Belfast BT7 3DF; John McCune Anderson, 16 Torgrange, Holywood, County Down, BT18 0NG; Eric Thomas McAdams, Ormsdale, 52 Cable Road, Whitehead, County Antrim, BT38 9PZ, all of Northern Ireland

[21] Appl. No.: 210,757

[22] Filed: Mar. 22, 1994

[30] Foreign Application Priority Data

Mar. 23, 1993 [IE] Ireland ................ 930230

[51] Int. Cl.⁶ .................................. A61B 5/04
[52] U.S. Cl. .......................... 128/639; 128/644
[58] Field of Search .................. 128/639–641, 128/644; 607/149, 152, 153

[56] References Cited

U.S. PATENT DOCUMENTS

| | | |
|---|---|---|
| 3,144,018 | 8/1964 | Head .............................. 128/644 |
| 3,741,219 | 6/1973 | Sessions . |
| 3,989,036 | 11/1976 | Sasamori . |
| 4,016,869 | 4/1977 | Reichenberger ................ 128/640 |
| 4,082,087 | 4/1978 | Howson ........................ 128/640 |
| 4,362,165 | 12/1982 | Carmon et al. ................ 128/640 |
| 5,058,589 | 10/1991 | Ding et al. .................... 128/640 |

FOREIGN PATENT DOCUMENTS

| | | |
|---|---|---|
| 0014341 | 8/1980 | European Pat. Off. . |
| 1128329 | 9/1968 | United Kingdom . |
| 1575364 | 9/1980 | United Kingdom . |
| 2160107 | 12/1985 | United Kingdom . |

Primary Examiner—Lee S. Cohen
Attorney, Agent, or Firm—Mintz, Levin, Cohn, Ferris, Glovsky and Popeo, P.C.

[57] ABSTRACT

A biosignal electrode device comprises a flexible electrically insulating substrate 11 having deposited thereon an electrically conductive layer forming an electrode sensor 14 and a lead 15 for the sensor. The portion of the substrate bearing the sensor is formed in relief such that the sensor stands above the surrounding substrate.

9 Claims, 4 Drawing Sheets

PROFILED BIOSIGNAL ELECTRODE DEVICE

BACKGROUND OF THE INVENTION

This invention relates to a profiled biosignal electrode device.

The skin's outermost layer, the stratum corneum, is composed of dead cells. It is relatively nonconductive and presents a high impedance to the transmission of bioelectric signals. Stratum corneum, due to its dielectric properties and thinness, permits capacitive coupling between a metal electrode placed on the skin surface and the underlying conductive tissues. Some ions manage to traverse the stratum corneum, and the flow of this ionic current can be represented electrically by a large resistance shunting the skin's capacitance. If the electrode-skin impedance is large relative to the input impedance of the amplifier, biosignal attenuation occurs. The presence of a reactive component in the electrode-skin impedance can also create filtering and, hence, distortion of the signal.

Another problem source is 50/60 Hz electric-field coupling between neighbouring powerlines and the patient's monitoring cables. This interference is due to electrode-skin impedance mismatch, which leads to a differential interference signal at the amplifier's input.

Variance in ionic concentration across the epidermis causes a potential difference. This potential has a typical value of 30 mV, with the skin surface normally negative relative to the inside of the body. This potential varies from site to site, patient to patient, and depends on the gel composition which is used in conjunction with the electrode and skin condition. Slight differences in electrode materials and skin-site parameters cause electrode-skin potentials to be mismatched. The difference between potentials will be amplified along with the desired biosignal. Fluctuations in the magnitudes of potentials and their difference can introduce an undesired frequency component into the desired signal, making accurate diagnosis difficult. The dependence of the electrode-skin potential on thickness of the epidermal layer is important in many biosignal recording applications. If that thickness is changed by stretching or pressing on the skin, the potential can vary by up to 10 mV. This is the major source of motion artefact (fluctuations in baseline trace with patient movement) and a function of the degree of skin deformation.

Many current electrodes incorporate electrolytic gels which serve to ensure an optimal electrical contact between the electrode sensor and the patient's skin and which also serve to decrease the high epidermal impedance.

The use of electrolytic gels not only decreases the skin's impedance, thus avoiding associated problems, but also has been observed to reduce motion artefact levels.

The potential disadvantages of using gelled electrodes reside in the utilization of the electrolyte gel which requires that such gel be extraneously supplied during application. Usually, the, gel is packed in a tube which must be squeezed for dispensing a charge thereof. Sometimes, a charge of gel is packaged separately to that of the electrode in an hermetically sealed container. In the former case, the necessity to provide extraneous gel during application is an obvious inconvenience, especially in the home-based environment under emergency conditions. Following use, the electrode (if it is reusable) and the application site must be cleaned.

In the latter case, once the package is opened to atmospheric conditions the gel will rapidly dry out. Even when properly packaged, the gelled electrode will have a relatively short shelf life. For home-based monitoring applications, for example, a sufficient supply of such pregelled disposable packages must be provided and must be periodically renewed.

A simple method of avoiding the above problem in, for example, the home-based monitoring environment, is to use a dry metal plate electrode or electrodes attached, for example, to a limb of the patient by means of elasticated straps. Although no gel is used, the accumulation of perspiration under the metallic plate will eventually moisten the skin covered by the 'dry' electrode. The initial impedance is however much higher than that for a gelled electrode and the impedance deceases relatively slowly with time. This need not be a major problem, however, as amplifiers now exist with input impedances and common-mode rejection ratios sufficiently high to cope with such large electrode-skin impedances.

The advantages of such electrolyte-free electrodes are numerous. The electrodes can be applied rapidly and with ease to a patient's limb as they do not require skin or electrode preparation prior to or after electrode application. The electrodes are reusable, pose no storage problems and there is little corrosion of the metal plate. Such electrodes have in the past proved optimal, for example, for low cost, rapid, mass screening of electrocardiograms.

Dry metal plate electrodes are however susceptible to 50/60 Hz interference problems due to the mismatching of their high electrode-skin impedances. They do not perform well on hairy subjects due to poor electrical contact. Even when firmly strapped to a part of the body, a rigid, metal plate electrode is prone to generate motion artefacts when the underlying 'dry' skin is stretched or moved or when the electrode is pressed. The relatively rigid plate electrode is only suitable as a limb electrode as it cannot easily be attached to a patient's chest, for example, and is incapable of accommodating body contours.

SUMMARY OF THE INVENTION

It is an object of the present invention to overcome these problems.

The invention, therefore, provides a biosignal electrode device comprising a flexible electrically insulating substrate having deposited thereon an electrically conductive layer forming an electrode sensor and a lead for the sensor, the portion of the substrate bearing the sensor being formed in relief.

Preferably, the surface of the sensor element is rough, textured, rippled, punctured or the like, all of which are hereinafter embraced by the word "rough".

The biosignal electrode device according to the invention may be manufactured by several well-known techniques including embossing, debossing or hydroform embossing. In the embossing or debossing processes, matching male and female die sets are used to form the material. As it is the male die projections which apply the initial pressure to the unsupported substrate, they give rise to unequal strains in the substrate which can distort the form shape. Problems with thermal expansion may be encountered with thermal forming processes and tooling temperature can cause damage to the inking systems. Accordingly, the preferred manufacturing technique is by way of hydroform embossing.

In hydroform embossing, one half of the conventional die set is eliminated and replaced with a hydraulic fluid cell assembly which has a urethane diaphragm face. Hydroform embossing therefore uses a single sided tool with the fluid cell assembly serving as the active compressive "counter-die". With hydroform embossing, hydrostatically equalized holding forces are applied to the entire die surface area and substrate before forming into the die cavity occurs. The substrate may therefore be stretched-formed into the cavity rather than gathering around male die projections and being forced or pinched into the female tool, with resulting damage to the substrate. A counter die in the form of an elastomer diaphragm will not mar the polymer substrate.

A further advantage of hydroform embossing is that the one sided tool can be created directly from photo-artworks and thus permits the accurate registration from the embossing artwork to the tool. The single sided tool also allows the substrate to be accurately pin-registered to the die plate.

With hydroform embossing, many unique embossing applications are possible which cannot be achieved by conventional techniques such as the forming of angular bends, the deep drawing of shapes and the creation of negative or zero draft angles on the formed part.

In order to provide the roughness in the surface of the sensor element the substrate and the conductive layer must be suitably malleable. Further, the coefficient of thermal expansion of the conductive layer should match that of the flexible substrate. The flexibility of the materials should be such as to minimise cracking, peeling etc.

The conductive layer may be provided by means of an electrically conductive ink which also has the property of "self protecting" against corrosion and residual growth on the surface.

A suitable thermoplastic material loaded, for example, with silver and silver-chloride particles may be used as the conductive layer. Appropriate choice of particle size, thermoplastic binder, deposition and curing parameters leads to an optimal conductive layer surface ensuring good electrical contact with the skin.

Moulded surface "ripples" or punctured "points" in the sensor further optimise contact between the sensor and the patient's skin. Due to frictional forces, the ripples or points minimise the movement of the electrode relative to the skin and thus ensure more stable biosignal recording. The ripples or points increase the contact area and, when pressed against the skin, penetrate the epidermal layer sufficiently to decrease significantly the electrode-skin potential fluctuations (motion artefact) without traumatising the skin.

The substrate surrounding the lead may be cut or otherwise removed in order to leave a finger of substrate on which is located the lead. Such a finger enables relative movement of the sensor and thus accommodates changes in the monitored body segment's dimensions and form due to breathing, patient movement etc.

Multiple electrode devices, referred to herein as "off-shoot" electrodes may be connected to a common electrode harness. The harness may be formed with multiple female connectors which may be made by hydroform embossing in areas of the harness substrate coated with a conductive layer. The off-shoot electrodes may then be connected by means of male connectors, also manufactured by hydroform embossing, to respective ones of the female connectors on the harness. The conductive layer forming the connecting lead on, for example, the obverse face of the "off-shoot" electrode is through-hole-plated to the reverse face of the substrate in order to make connection with the electrode sensor. This method of connection enables the off-shoot electrode to pivot about the connector enabling the electrode device to accommodate anatomical inter-human variations. Several sections incorporating male and female connectors at each end may be connected in series in order to produce articulated off-shoot electrodes which have a high degree of manoeuvrability. Good electrical contact can be ensured by: (i) providing a tight male-female connector fit; (ii) by roughening the connecting surfaces of the male and female connectors during the forming process; and (iii) by depositing conductive layers at the connector sites which have rough surfaces due, for example, to the particle size of the filler.

The conductive layer may be printed or otherwise deposited onto the substrate as required for a given application. Where there are multiple sensors the sensors may be backed by a band of, for example, suitable foam in order to (i) keep the sensor elements in their correct relative positions when the surrounding substrate is removed (ii) make the electrode device more manageable and avoid lead entanglement (iii) help distribute any applied pressure evenly over the electrodes and (iv) thus help minimise motion artefact. The backing layer should preferably be lightweight, flexible and stretchable to ensure that the harness is comfortable, that it can conform readily with body contours and that it can accommodate changes in the body segment's dimensions due to breathing or patient movement.

The electrode device according to the invention may be applied manually by the subject or clinician to the part of the body under study in applications which only require the short term, "diagnostic" observation of the detected biosignal(s) and without the need for a gel layer. For longer term monitoring applications an electrode harness comprising a plurality of electrode sensor elements may be held in place on the required body part by means of elasticated straps, adhesive tape, suction cups etc. and again without the need for a gel layer.

The electrode device according to the invention when in the form of a harness may be gelled, preferably with hydrogel pads, for certain biomedical applications. "Solid", conductive, adhesive hydrogel pads can be coated onto the profiled printed sensors, giving rise to a simple, easy-to-manufacture electrode structure. The use of such hydrogel dispense with the need for the gel-retaining ring, gel-impregnated sponge and sealing cap used in current 'wet ' gel electrodes.

The use of adhesive hydrogel on the electrode device according to the invention is advantageous in applications where, for example, large numbers of electrodes must be applied to the body. Body surface cardiac mapping is one such application. The number and distribution of the electrodes is such that it would be difficult to hold dry electrodes sufficiently well, manually or by means of straps, to ensure good electrical contact.

The roughened surface of the electrode sensor element ensures firm electrical contact between the sensor and the gel pad as well as increasing the contact area and thus decreasing the sensor-gel interface impedance. That part of the electrode device having the electrode sensor element thereon may be contoured during the embossing technique in such a way as to form a recess around the sensor element which is surrounded by a lip and into which recess gel may be loaded. The recess would enable gel, while in a fluid state, to be poured onto the profiled sensor and cured in situ. Following the application of the gel into the recesses, a removable backing strip may be set in place so as to retain the integrity of the gel prior to use. The electrode device according to the invention when in the form of a harness enables a plurality of sensor elements to conform optimally with the body's contours.

BRIEF DESCRIPTION OF THE DRAWINGS

The invention will be understood in greater detail from the following description of preferred embodiments thereof given by way of example only and with reference to the accompanying drawings in which.

DETAILED DESCRIPTION OF THE PREFERRED EMBODIMENTS

Figure 1:
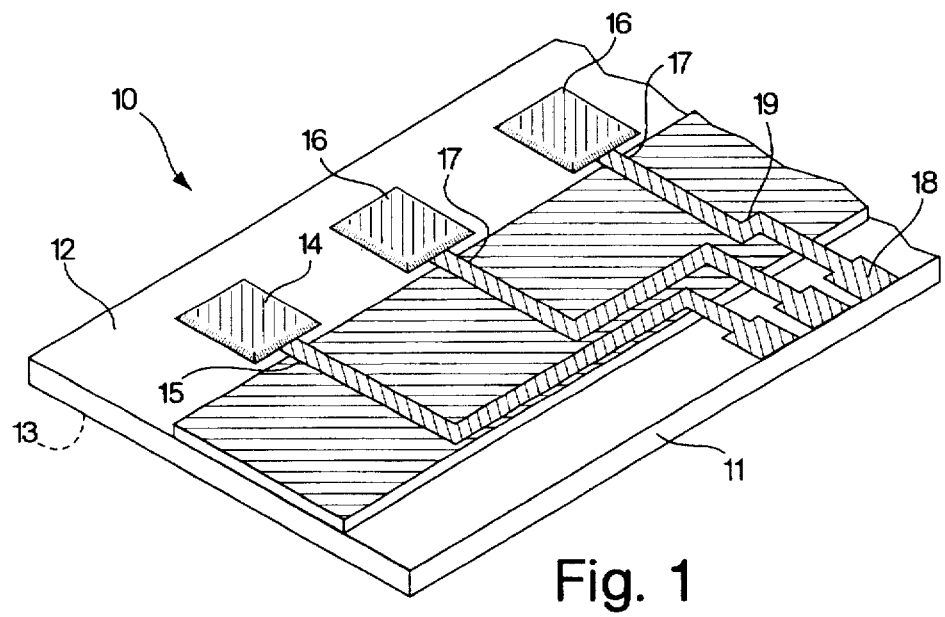
FIG. 1 is a perspective view of a first embodiment of a biosignal electrode according to the invention.

Referring now to the drawings, and in particular to FIG. 1 thereof, there is shown a first embodiment of an electrode device 10 according to the invention which comprises a substrate 11 having an obverse face 12 and a reverse face 13. Onto the obverse face 12 is deposited an electrode sensor 14 and an associated lead 15. Additional sensors 16 and respective associated leads 17 may also be deposited on to the obverse face 12 or the reverse face 13 if desired. Each of the leads 15, 17 terminates in a respective connector end 18. The sensors 14, 16; leads 15, 17; and connector ends 18 may be deposited by well-known techniques including screenprinting of a suitable electrically conductive ink. A dielectric layer 19 is deposited over the leads 15, 17 in order to insulate them from a patient on which the device 10 will be used. It will be appreciated that the sensors 14, 16 and the connector ends 18 are allowed to remain exposed. The parts of the substrate 11 having the sensors 14, 16 thereon are in relief relative to the remainder of the substrate 11. To provide for such relief, the substrate may be subject to well-known techniques such as profiling, embossing, forming, moulding or casting. A preferred technique is that of hydroform embossing as discussed earlier in the present specification.

Figure 2:
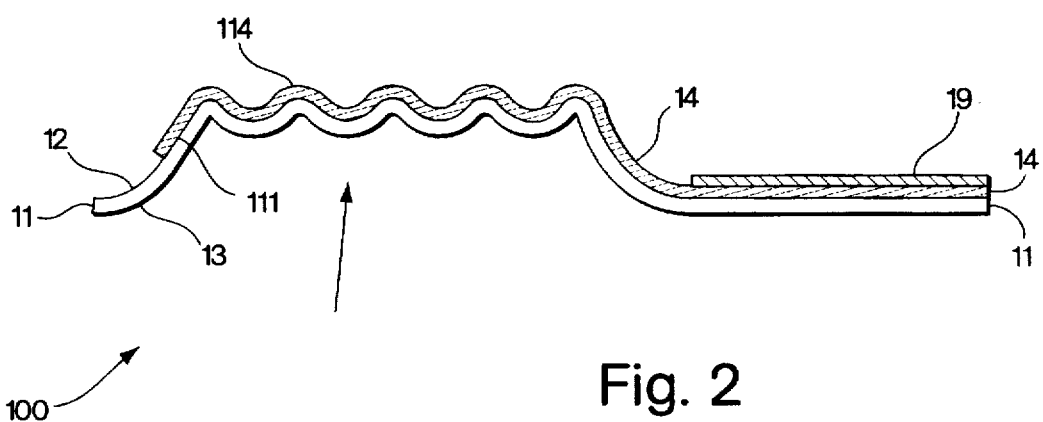
FIG. 2 is a cross-sectional view of a second embodiment of a biosignal electrode according to the invention.

In FIG. 2 of the drawings, there is shown a second embodiment of an electrode device 100 according to the invention which is substantially similar to the electrode device 10 save as follows. That part 111 of the substrate 11 which is in relief is rippled or indented and consequently the electrode sensors 14, 16 are also rippled or indented at 114 thereby giving rise to a rough or textured surface to the electrode sensors 14, 16.

Figure 3:
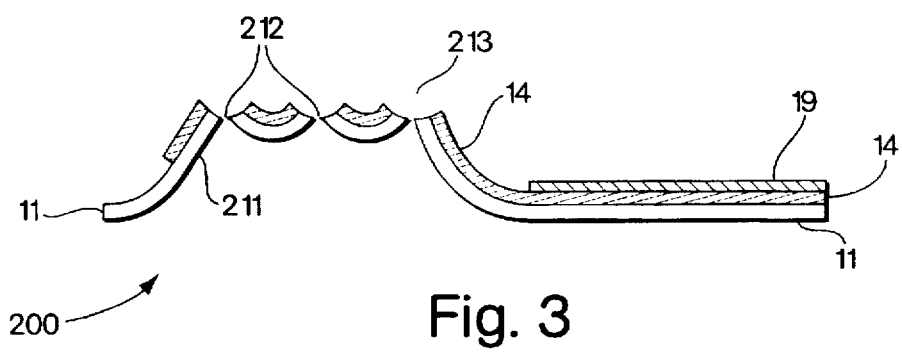
FIG. 3 is a cross-sectional view of a third embodiment of a biosignal electrode according to the invention.

In FIG. 3 of the drawings, there is shown a third embodiment of an electrode device 200 according to the invention which is substantially similar to the electrode device 10 except as follows. The part 211 of the substrate 11 which is in relief is punctured with a plurality of relatively small openings 212 which give rise to a plurality of fine points 213 on the electrode sensors 14, 16.

The use of a thin, flexible substrate 11, and dielectric layer 19 layers gives rise to a flexible overall electrode device according to the invention capable of conforming with the body's contours. The protrusion of the electrode sensor 14, 16, further optimises the contact between the electrode sensors 14,16 and the subject's skin when the device 10 is applied to the skin. With the electrode sensors 14,16 in relief, there is provided the additional advantageous feature of absorbing the effects of variations in pressure on the device according to the invention when in use and thus help minimise motion artefacts which are generally a major problem with dry electrode structures.

Figure 4:
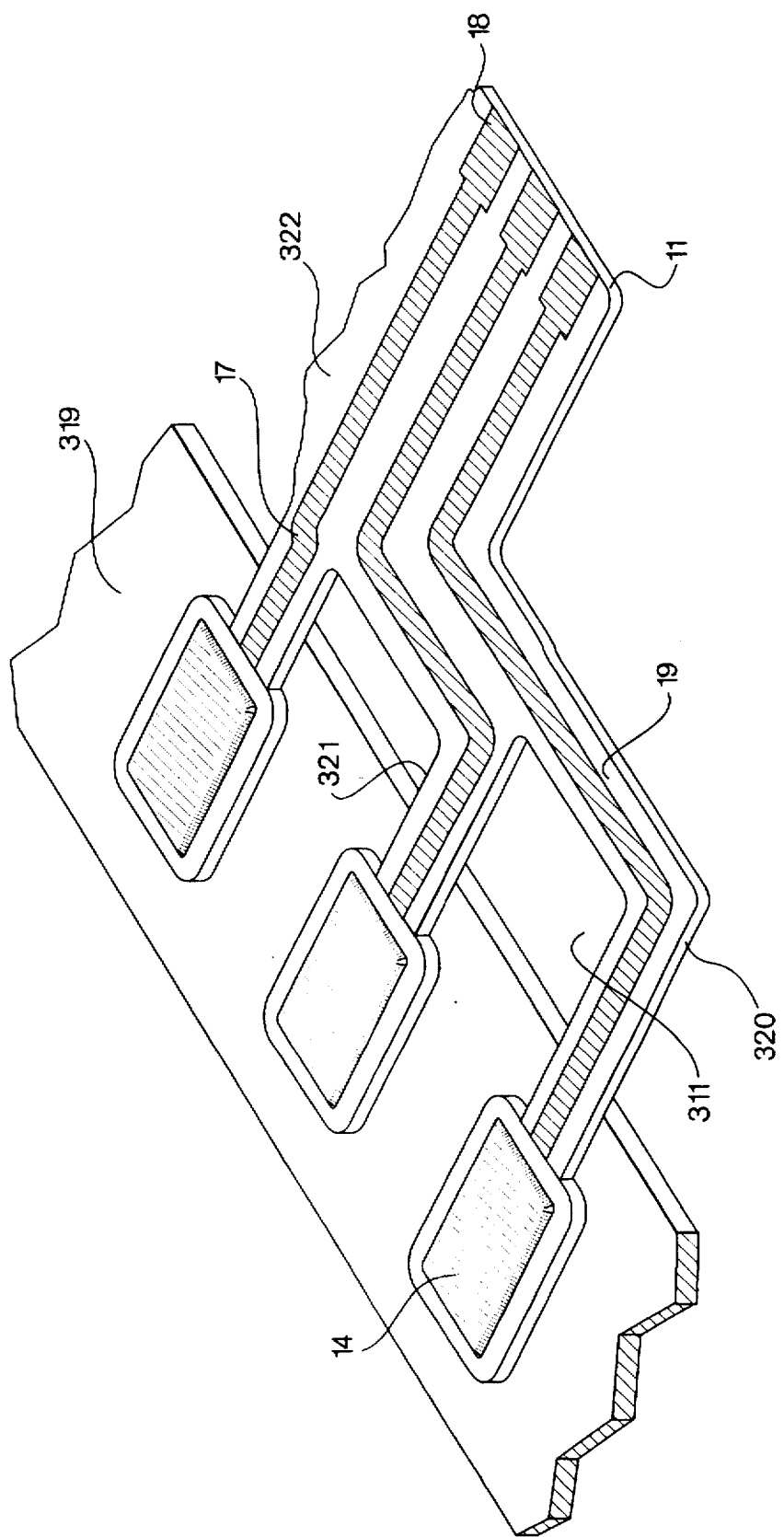
FIG. 4 is a perspective view of a fourth embodiment of a biosignal electrode according to the invention.

In FIG. 4 of the drawings, there is shown a fourth embodiment of a device 300 according to the invention which is substantially similar to the device 10 of FIG. 1 of the drawings and which may have the additional features as described with respect to devices 100 or 200 except as follows.

The part of the substrate 311 which surrounds the leads 17 may be cut or otherwise removed in order to leave fingers 320, 321, 322 of substrate on which are located the leads 17. The provision of the fingers 320, 321, 322 enables movement of the sensor elements 14, 16 relative to the connector ends 18 and thus accommodates movement of the subject due, for example, to breathing etc.

The sensors 14, 16 and associated leads 15 may be printed or otherwise deposited onto the substrate 11 at the required relative distances and orientations for a given application. Where possible, the sensors 14, 16 may be backed by a band 319 of, for example, suitable foam in order to (i) keep the sensors 14, 16 in their correct relative positions when the surrounding substrate 11 is removed (ii) make the electrode device 300 more manageable and avoid lead entanglement (iii) help distribute any applied pressure evenly over the sensors 14, 16 and (iv) thus help minimise motion artefact. The band 319 should preferably be lightweight, flexible and stretchable to ensure comfort; conformity with body contours; and to enable changes in the body segment's dimensions due to breathing or patient movement to be accomodated.

Figure 5:
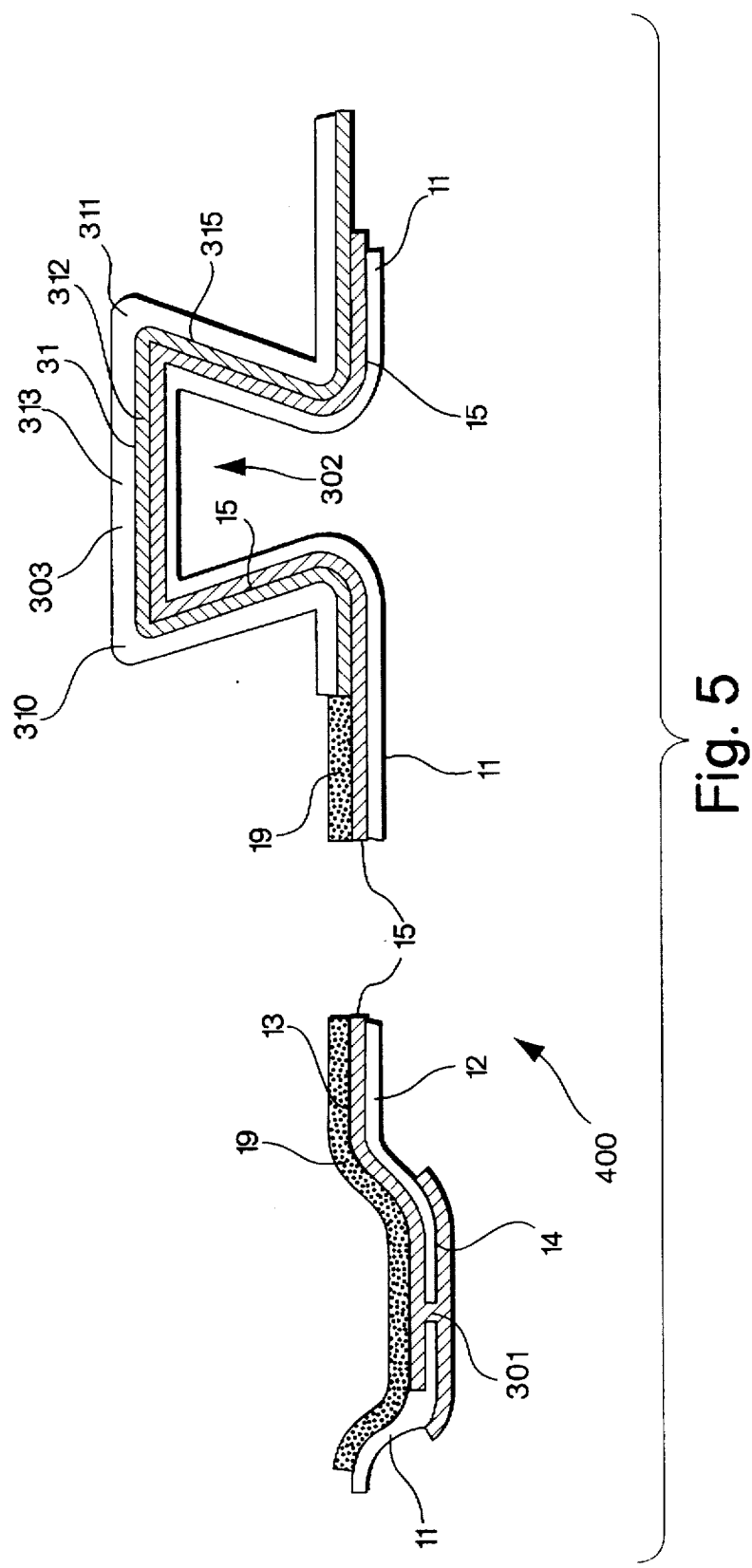
FIG. 5 is a cross-sectional view of a fifth embodiment of a biosignal electrode according to the invention.

In FIG. 5 of the drawings which relates to an "off-shoot" electrode, there is shown a fifth embodiment 400 of an electrode device according to the invention which is substantially similar to the device 10 of FIG. 1 of the drawings except as follows. First, it comprises only a single sensor 14 and lead 15. Second, the lead 15 is absent from the obverse face 12 being, instead, deposited on the reverse face 13. The lead 15 is in electrical communication with the sensor 14 having regard to the provision of a hole 301 in the substrate 11 which enables the electrically conductive ink to flow through the hole 301 thereby providing electrical communication between the sensor 14 and the lead 15. Further, the end of the substrate 11 which is remote from the end having the sensor 14 thereon is formed into a u-shape in a direction opposite to that of the substrate 11 on which the sensor 14 is deposited to provide a male connector 302. The reverse face 13 of the substrate 11 having the male connector 302 thereon also has a continuation of the lead 15 thereon.

A harness 310 is provided which essentially comprises a substrate 311 also having an obverse face 312 and a reverse face 313. The harness has a plurality of shapes in the form of female connectors 303 which are engageable with respective male connectors 302.

The obverse face 312 of the harness 310 has a lead 315 deposited thereon in a manner similar to that of the lead 15. The lead 315 extends into the female connector 303 so that when the connectors 302 and 303 are mating as shown in FIG. 5, there is electrical connection between the leads 15 and 315. The lead 315 may terminate on the harness 310 in a manner similar to the connector end 18. It will be appreciated that the harness 310 will have a plurality of leads 15 in electrical isolation from each other to enable a plurality of off-shoot electrode devices to be connected to the harness so that the harness 310 not only provides a means for enabling a plurality of electrode devices to be attached to the body of a patient or subject but also to provide an independent electrical lead from each electrode device the ends of which leads may be individually electrically connected to a suitable monitoring device.

Figure 6:
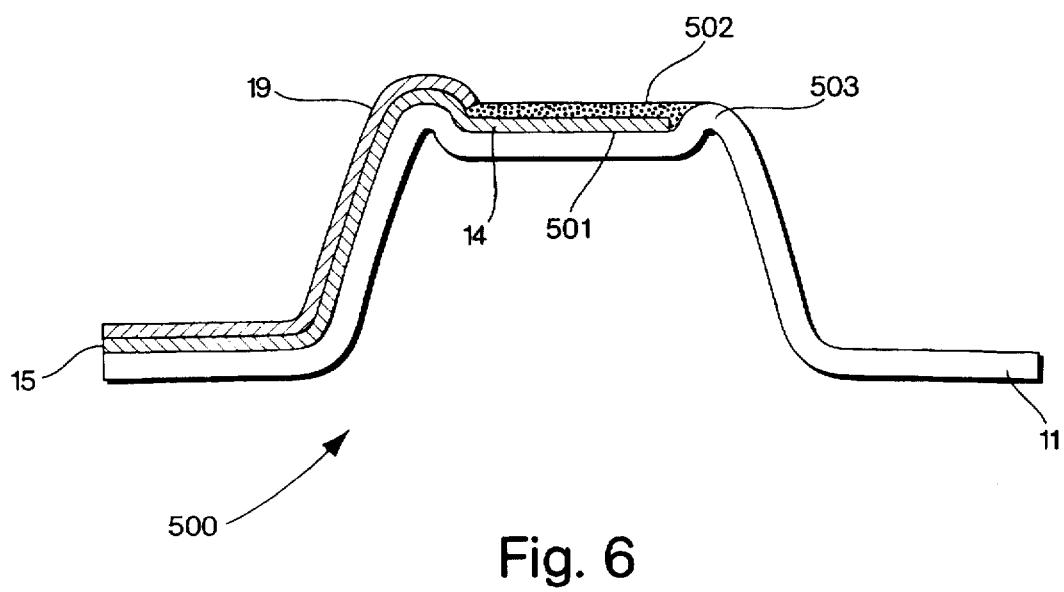
FIG. 6 is a cross-sectional view of a sixth embodiment of a biosignal electrode according to the invention.

In FIG. 6 of the drawings, there is shown a sixth embodiment of an electrode device 500 according to the invention which is essentially similar to the device shown in FIG. 1 of the drawings except as follows. That part of the substrate 11 having the sensor 14 thereon which is in relief is provided with a well 501 having a lip 503 and in which the sensor element 14 is located. Following the manufacture of the electrode device, a suitable electrolytic gel 502 is poured into the well 501 which, depending on the type of gel used, cures to a viscous consistency. There is then applied to the well 501 or more preferably a plurality of wells a backing strip which is removable prior to the use of the device.

The invention is not limited by or to the specific embodiment described which can undergo considerable variation without departing from the scope of the invention.

We claim:

1. A biosignal electrode device, comprising:
   a) a flexible, electrically insulating substrate, and
   b) an electrically conductive layer deposited on a surface of said substrate, and forming thereon an electrode sensor for contacting a patient's skin, and a lead for the sensor,
   c) wherein a portion of the substrate bearing the sensor is formed in relief such that said substrate portion and attendantly the sensor are upstanding from surrounding substrate.

2. A device as claimed in claim 1, wherein the surface of the sensor is roughened.

3. A device as claimed in claim 1, wherein the lead is deposited on an opposite surface of the substrate from the sensor, and is connected to the sensor through an aperture in the substrate.

4. A device as claimed in claim 1, wherein the portion of the substrate which is in relief and bears the sensor is slightly recessed to form a well, and the well contains an electrolytic gel.

5. A device as claimed in claim 1, wherein there is a plurality of sensors and associated leads are provided on the substrate.

6. A device as claimed in claim 5, wherein regions of the substrate between the sensors and leads are removed to provide fingers of substrate, each bearing a sensor and an associated lead.

7. A device as claimed in claim 5, wherein the sensors are backed by a flexible and stretchable band of insulating material.

8. A device as claimed in claim 1, wherein a portion of the substrate remote from the sensor is formed into one part of a male/female connector having an electrically conductive layer thereon which is electrically connected to the lead.

9. A biosignal electrode assembly comprising a harness in the form of an electrically insulating substrate having a plurality of leads deposited thereon each terminating in one part of a male/female connector, and a plurality of biosignal electrode devices as claimed in claim 8 each connectable by its connector part to a respective connector part on the harness.

* * * * *